US008563046B2

(12) United States Patent
Harrison et al.

(10) Patent No.: US 8,563,046 B2
(45) Date of Patent: Oct. 22, 2013

(54) COMPOSITIONS, SYSTEMS, AND/OR METHODS INVOLVING CHLORINE DIOXIDE ("CLO2")

(75) Inventors: Ken Harrison, Madison, VA (US); Nick Blandford, Charlottesville, VA (US)

(73) Assignee: Dharma IP, LLC, Charlottesville, VA (US)

(*) Notice: Subject to any disclaimer, the term of this patent is extended or adjusted under 35 U.S.C. 154(b) by 593 days.

(21) Appl. No.: 12/192,371

(22) Filed: Aug. 15, 2008

(65) Prior Publication Data

US 2009/0053326 A1    Feb. 26, 2009

Related U.S. Application Data

(60) Provisional application No. 60/965,870, filed on Aug. 23, 2007.

(51) Int. Cl.
*A01N 59/02* (2006.01)
*A61K 33/20* (2006.01)

(52) U.S. Cl.
USPC ........................................................ 424/661

(58) Field of Classification Search
None
See application file for complete search history.

(56) References Cited

U.S. PATENT DOCUMENTS

| 5,165,910 | A | * | 11/1992 | Oikawa et al. ................ 423/477 |
| 5,380,517 | A | | 1/1995 | Sokol |
| 5,403,828 | A | | 4/1995 | Lewis |
| 5,741,757 | A | | 4/1998 | Cooper |
| 5,814,312 | A | | 9/1998 | Reich et al. |
| 5,840,268 | A | | 11/1998 | Ikegami |
| RE36,064 | E | | 1/1999 | Davidson |
| 5,855,861 | A | | 1/1999 | Lee |
| 6,033,641 | A | | 3/2000 | Hall |
| 6,046,243 | A | | 4/2000 | Wellinghoff |
| 6,051,135 | A | | 4/2000 | Lee |
| 6,131,774 | A | | 10/2000 | Thomas |
| 6,238,643 | B1 | | 5/2001 | Thangaraj |
| 6,358,935 | B1 | | 3/2002 | Beck |
| 6,468,479 | B1 | | 10/2002 | Mason |
| 6,582,682 | B2 | | 6/2003 | Stier |
| 6,689,378 | B1 | | 2/2004 | Sun et al. |
| 7,229,647 | B2 | | 6/2007 | Lee |
| 7,416,326 | B2 | | 8/2008 | Sakata |
| 7,467,633 | B2 | | 12/2008 | Smith |
| 7,678,388 | B2 | | 3/2010 | Mason |
| 2002/0192340 | A1 | | 12/2002 | Swart |
| 2004/0137202 | A1 | | 7/2004 | Hamilton |
| 2004/0175435 | A1 | | 9/2004 | Beck |
| 2005/0218054 | A1 | | 10/2005 | Sakata |
| 2005/0224750 | A1 | | 10/2005 | Yang |
| 2005/0272606 | A1 | | 12/2005 | Manchak |
| 2006/0006361 | A1 | | 1/2006 | Callerame |
| 2007/0224233 | A1 | | 9/2007 | Maekawa |
| 2008/0023668 | A1 | | 1/2008 | Callerame |
| 2008/0181973 | A1 | | 7/2008 | Lee |
| 2009/0105323 | A1 | | 4/2009 | Bliss |

FOREIGN PATENT DOCUMENTS

| CA | 2680934 | 9/2008 |
| CN | 1166362 | 12/1997 |
| CN | 1820607 | 8/2006 |
| JP | 91000979 | 1/1991 |
| JP | H0300979 | 1/1991 |
| JP | 2532887 | 6/1996 |
| JP | 2532887 | 9/1996 |
| JP | 11506308 | 6/1999 |
| JP | 2003326277 | 11/2003 |
| JP | 2006-2044 | 8/2006 |
| JP | 2006-204445 | 8/2006 |
| JP | 2007217239 | 8/2007 |
| WO | WO9624388 | 8/1996 |
| WO | WO00/12137 | 3/2000 |
| WO | WO03/093170 | 11/2003 |

OTHER PUBLICATIONS

Kennaugh, J. Nature 1957, 160, 238.*
Masschelein (I&EC Product Research and Development 1967, 6, 137-142).*
Kennaugh (Nature 1957, 160, 238).*
Wimmer, "Cyclodextrins—From Ullmann's Encyclopedia of Industrial Chemistry", Jan. 15, 2003, 9 pages, Wiley-VCH Verlag GmbH & Co. KGaA, Weinheim.
Coope, "Electron Spin Resonance Study of ClO2 and Cl2—Adsorbed on Zeolites", 1971, Molecular Physics, 21(6), 1043-1055.
Pietrzak, "Preferred Rotation of ClO2 adsorbed on CaX and Synthetic Zeiolites", Jun. 30, 1972, Molecular Physic, 24(4), 909-911.
Shimokoshi, "Electron Spin Resonance Study of Chlorine Dioxide Adsorbed on the Alkali-Cation-Exchanged X-Type Zeolites", 1974, Journal of Physical Chemistry, 78(17), 1770-1771.
Sugihara, "Effect of Exchanged Cations upon the Electron Spin Resonance Hyperfine Splitting of Chlorine Dioxide Adsorbed on X-Type Zeolites", 1977, Journal of Physical Chemistry, 87(7), 669-673.
Hedges, "Industrial Applications of Cyclodextrins", May 27, 1998, 10 page(s), Chem. Rev. 1998, 2035-2044.
Xing, "Abstract of "Study on Controlled Release Chlorine Dioxide Microcapsules"", Jan. 1, 2004, Anhui Ligong Daxue Xuebao Bianjibu, 24 (2), 52-55, People's Republic of China.
Click, "Techniques of Histo- and Cytochemistry", 1949, 470 pages, Interscience Publishers, Inc.; available online at http://www.archive.org/stream/techniquesofhist031071mbp/techniquesofhist031071mbp_djvu.txt.
Grandcircuitinc.com, "Overview of Chlorine Dioxide (ClO2)", Aug. 31, 2001, 17 pages, http://www.grandcircuitinc.com/Howard%20Alliger%20-%20An%20Overall%20View%20Cl02.pdf.

(Continued)

*Primary Examiner* — James H. Alstrum-Acevedo
*Assistant Examiner* — Jessica Kassa
(74) *Attorney, Agent, or Firm* — Michael Haynes PLC; Michael N. Haynes

(57) ABSTRACT

Certain exemplary embodiments can provide a composition of matter comprising chlorine dioxide dissolved in acetic acid. When stored, a concentration of the chlorine dioxide in the composition of matter can be retained, with respect to an initial concentration of chlorine dioxide in said composition of matter, at, for example, greater than 30% for at least 28 days. Certain exemplary embodiments can provide a method comprising releasing chlorine dioxide from a composition comprising chlorine dioxide dissolved in acetic acid.

22 Claims, 2 Drawing Sheets

(56) References Cited

OTHER PUBLICATIONS

Gray, "The Microtomist's Formulary and Guide", 1954, 1096 pages, The Blakiston Company, Inc.; available online at http://www.archive.org/stream/microtomistsform00gray/microtomistsform00gray_djvu.txt.

Kroshcwitz, editor, "Kirk-Othmer Encyclopedia of Chemical Technology, 4th Ed. vol. 5", 1993, p. 972, John Wiley & Sons, Inc., New York, NY.

Richards, "Studies on Arthropod Cuticle. II. Electron Microscope Studies of Extracted Cuticle", Jun. 1, 1948, pp. 212-235, The Biological Bulletin/Marine Biological Laboratory.

Tchobanoblous & Burton, "Wastewater Engineering: Treatment, Disposal, and Reuse, 3rd Edition", Jan. 1, 1991, p. 50-51, Metcalf & Eddy, Inc. McGraw-Hill, Inc.

Totze, "Diaphanol and other chlorine dioxide solutions in zoological microtechnology; Certified German-to-English translation", Jan. 1, 1993, Mikrokosmos, vol. 27.

Chemical Abstracts Service, "Chemical Abstracts, vol. 49, No. 5", Mar. 10, 1955, The American Chemical Society, p. 5213.

Chemical Abstracts Service, "Chemical Abstracts, vol. 51, No. 21", Nov. 10, 1957, The American Chemical Society, p. 16609.

Wang Yufeng, Xing Honglong, "A Study on Sustained Release Chlorine Dioxide Microcapsules", Jun. 1, 2004, 9 pages with translation, Journal of Anhui University of Science and Technology (Natural Science) vol. 24 No. 2.

Copes, "Activity of Chlorine Dioxide in a Solution of Ions and pH Against *Thielaviopsis basicola* and *Fusarium oxysporum*", Jan. 1, 2004, 7 pages, Plant Disease vol. 88 No. 2; American Phytopathological Society.

Franson (Managing Editor), "Standard Methods for the Examination of Water and Wastewater, 20th Ed.", Jan. 1, 1998, pp. 4-73-4-79, APHA, Washington D.C.

Mebalds, "Using Ultra Violet Radiation and Chlorine Dioxide to Control Fungal Plant Pathogens in Water", Jan. 1, 1996, 2 pages, The Nursery Papers, Issue 1996-005.

OxyChem, "Laboratory Preparations of Chlorine Dioxide Solutions—Technical Data Sheet", Dec. 22, 2006, 4 pages.

Apolonatos, "Gas Adsorption with Molecular Sieve Zeolites", Jan. 1, 1990, 188 pages, Thesis, Univ. of Ottawa.

Payra, "Zeolites: A Primer; in Handbook of Zeolite Science and Technology; Chapter One", Jan. 1, 2003, 19 pages, CRC Press.

\* cited by examiner

COMPOSITIONS, SYSTEMS, AND/OR METHODS INVOLVING CHLORINE DIOXIDE ("CLO2")

CROSS-REFERENCE TO RELATED APPLICATIONS

This application claims priority to, and incorporates by reference herein in its entirety, U.S. Provisional Patent Application 60/965,870, filed 23 Aug. 2007. This application incorporates by reference herein in its entirety co-pending U.S. Non-Provisional patent application Ser. No. 12/183,523, filed 31 Jul. 2008.

BRIEF DESCRIPTION OF THE DRAWINGS

A wide variety of potential practical and useful embodiments will be more readily understood through the following detailed description of certain exemplary embodiments, with reference to the accompanying exemplary drawings in which.

DETAILED DESCRIPTION

Figure 1:
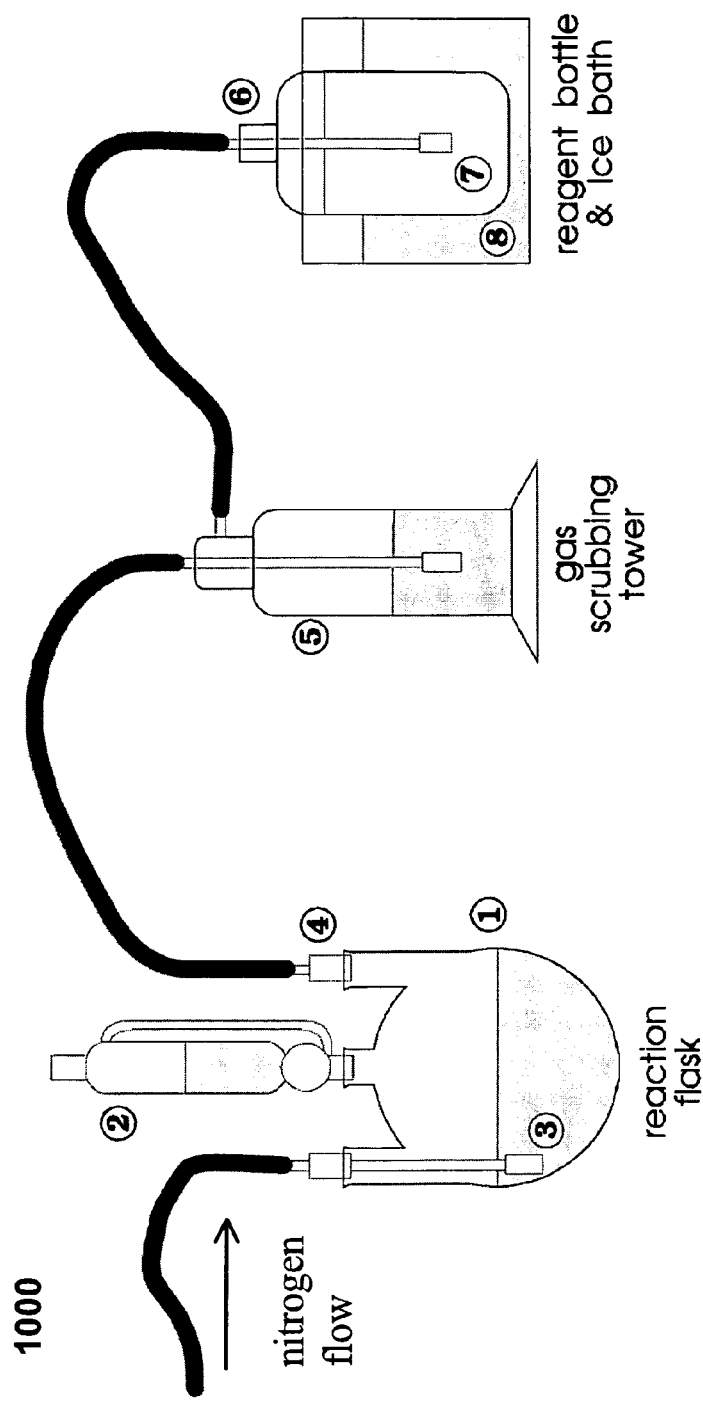
FIG. 1 is a block diagram of an exemplary embodiment of a method 1000.
Figure 2:
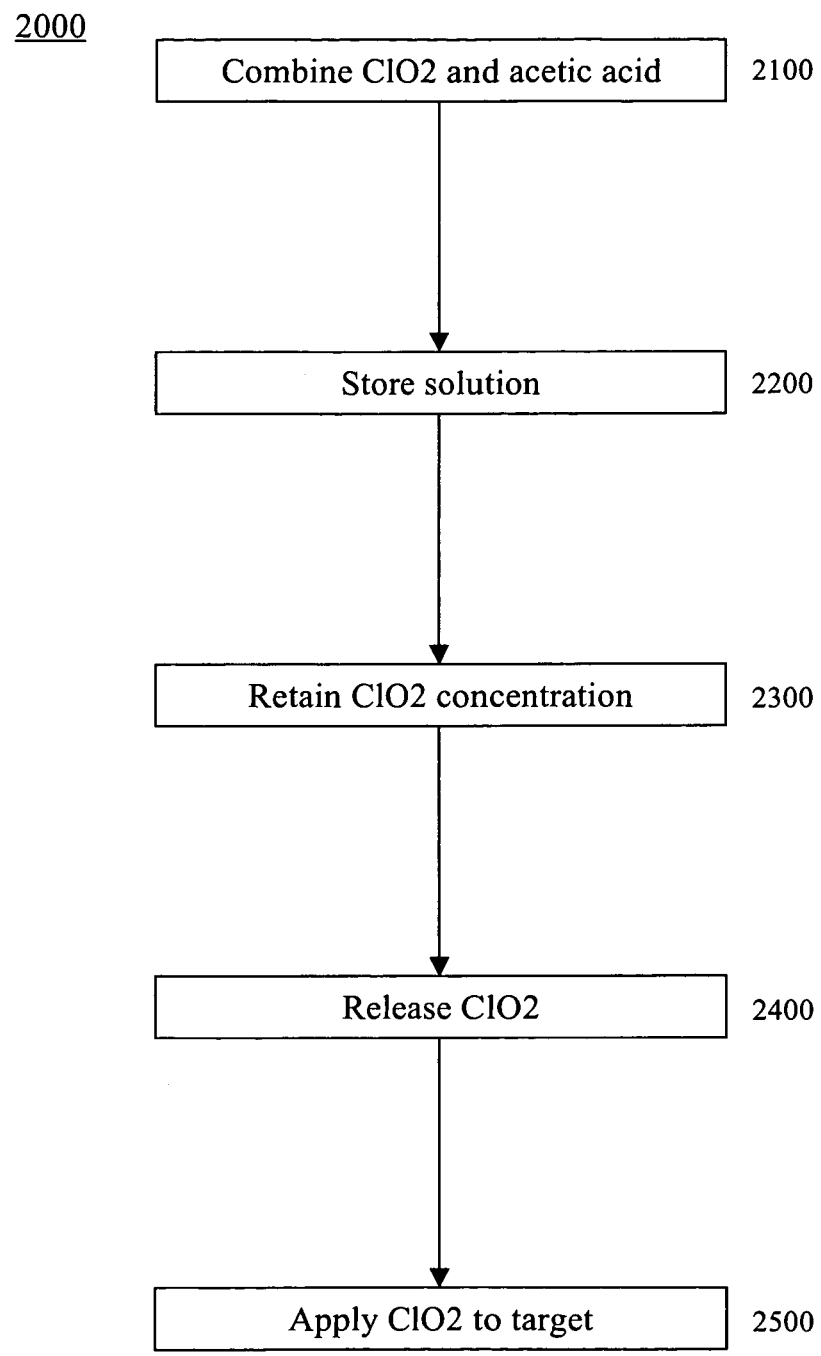
FIG. 2 is a flowchart of an exemplary embodiment of a method 2000.

Chlorine dioxide ("ClO2") can be an excellent disinfectant, and/or can be effective against a wide range of organisms. For example, ClO2 can provide excellent control of viruses and bacteria, as well as the protozoan parasites *Giardia, Cryptosporidium*, and/or amoeba *Naegleria gruberi* and their cysts.

In addition to disinfection, ClO2 can have other beneficial uses in water treatment, such as color, taste and odor control, and removal of iron and manganese. There are also important uses outside of water treatment, such as bleaching pulp and paper (its largest commercial use), disinfection of surfaces, and sanitization/preservation of fruits and vegetables.

ClO2 can present certain challenges, which can stem largely from its inherent physical and chemical instability. ClO2 in pure form is a gaseous compound under normal conditions. As a gas, it can be sensitive to chemical decomposition, exploding at higher concentrations and when compressed. Because ClO2 can be highly soluble in water, ClO2 can be used as a solution of ClO2 gas dissolved in water.

However, although ClO2 is somewhat soluble in certain solvents other than water, non-aqueous solutions of ClO2 have been used relatively little. We are not aware of any non-aqueous solvents being used to store ClO2 for significant time periods. ClO2 is often described as being highly reactive with organic compounds, which would include organic solvents. We have found that ClO2 at about 1000 ppm is stable in pure acetic acid (which is also known as ethanoic acid, and/or can be represented as CH3COOH and/or C2H4O2) for a period of at least 22 weeks at room temperature and at 120° F., with a retention of 90%. The solution can be conveniently prepared by bubbling a stream of gaseous ClO2 in nitrogen through the acetic acid, allowing the ClO2 to dissolve in the acetic acid and the nitrogen to simply vent.

Because of the physical and chemical instability of ClO2 mentioned above, virtually all commercial applications to date have required that ClO2 be generated at the point of use to deal with these challenges. However, on-site generation also can have significant draw-backs, particularly in the operational aspects of the equipment and the need to handle and store hazardous precursor chemicals. It can be desirable to have additional forms of ready-made ClO2.

Certain exemplary embodiments can provide a composition of matter comprising a solution of chlorine dioxide dissolved in acetic acid. When stored, a concentration of the chlorine dioxide in the composition of matter can be retained, with respect to an initial concentration of chlorine dioxide in said composition of matter, at, for example, greater than 30% for at least 28 days, greater than 80% for at least 150 days, and/or greater than 90% for at least 100 days. Certain exemplary embodiments can provide a method comprising releasing chlorine dioxide from a solution comprising ClO2 dissolved in acetic acid.

Certain exemplary embodiments can provide a solution formed by combining ClO2 with acetic acid, methods of forming the solution, and/or methods of using the solution as a means of delivering ClO2, such as essentially instantly delivering ClO2.

ClO2 is widely considered to be inherently unstable. Also, ClO2 is widely considered to be reactive with a fairly wide range of organic compounds, including organic solvents of which acetic acid is an example. It is reasonable to assume that ClO2 will react with acetic acid.

Chlorine dioxide can be generated by the method described in the OxyChem Technical Data Sheet "Laboratory Preparations of Chlorine Dioxide Solutions—Method II: Preparation of Reagent-Grade Chlorine Dioxide Solution", using nitrogen as the stripping gas.

That method specifies the following equipment and reagents:
three-neck reaction flask, 1-liter (1)
pressure equalizing addition funnel, 125-mls (2)
gas inlet tube, with adapter (3)
gas exit adapter (4)
gas scrubbing tower, 1-liter (5)
amber reagent bottle, 1 liter (6)
gas inlet tube, without adapter (7)
ice bath (8)
flexible tubing (rubber or Tygon®)
Technical Sodium Chlorite Solution 31.25
concentrated sulfuric acid, 36N That method specifies, inter alia, the following procedure:
Assemble the generator setup as shown in FIG. 1. To ensure airtight assembly use standard taper glassware and silicon grease if possible. Rubber stoppers are an acceptable alternative.

Fill the reaction flask and gas scrubbing tower with 500 mls of approximately 2.5% (wt) NaClO2 solution. Make certain all gas inlets are submerged. (2.5% NaClO2 solution may be prepared by diluting OxyChem Technical Sodium Chlorite Solution 31.25 1:10 with DI water).

Prepare 50 mls of 10% (vol) sulfuric acid solution and place this solution in the addition funnel. WARNING: Always add acid to water; never add water to acid.

Fill the amber reagent bottle with 500 to 750 mls. of DI water and place in an ice bath.

Turn on the air flow to the generation setup (there should be bubbles in all three solutions.) If there are not, check the setup for leaks.

Once there are no leaks, slowly add the acid solution (5 to 10 mls at a time). Wait 5 minutes between additions. Continue the air flow for 30 minutes after the final addition.

Store the chlorine dioxide solution in a closed amber bottle in a refrigerator. Properly stored solutions may be used for weeks, but should be standardized daily, prior to use, by an approved method, such as Method 4500-ClO2, Standard Methods for the Examination of Water and Wastewater., 20th Ed., APHA, Washington, D.C., 1998, pp 4-73 to 4-79.

We have unexpectedly discovered that, by bubbling sufficiently pure gaseous ClO2 diluted in nitrogen (as generated by this method) at a rate of, for example, approximately 100 ml/minute to approximately 300 ml/minute, through glacial acetic acid in place of plain water, at or below room temperature, a stable solution formed. (Acetic acid freezes at 62° F., so it should only be chilled, if at all, to temperatures which avoid freezing it. Cooling is not necessary, but may be advantageous for attaining higher ClO2 concentrations.) Concentrations from approximately 10 ppm to approximately 2000 ppm ClO2 have been prepared; it is expected that at least somewhat higher, and perhaps much higher, concentrations could be prepared without problems.

Alternatively, nitrogen can be bubbled through a solution of ClO2 in water, prepared by the above method or any other suitable method. The resulting stream of gaseous ClO2 in nitrogen can be bubbled through acetic acid as above, providing a solution of ClO2 in acetic acid. Essentially any means of bubbling gaseous ClO2 in an essentially inert gas stream through acetic acid will provide the solution of ClO2 in acetic acid.

The resulting solution of ClO2 in acetic acid is clear yellow. ClO2 content was determined by use of the Hach DR 2800 spectrophotometer, using one of its direct reading programs for ClO2 measurement. Before measurement, the sample was diluted 1:10 with ultrapure water, resulting in minimal background signal. To assure that the measurements were not significantly influenced by decomposition products absorbing at the measurement wavelength, the following experiment was conducted. A sample which had been stored for 180 days at 120° F., followed by 100 days at 105° F., was sparged with N2 to remove volatile components. At that point there was virtually no visible yellow color remaining, and the spectrophotometric measurement for ClO2 was negligible.

Glacial acetic acid is a somewhat hazardous material in its own right, and must be handled with caution. On the other hand, solutions of acetic acid in water at concentrations up to about 10% can be handled with minimal precautions. Based on results with ClO2 in glacial acetic acid, it was considered that acetic acid might confer an unusual level of stability to aqueous solutions of ClO2. It was found that solutions of 2000 ppm ClO2 in 10% aqueous acetic acid stored at 120° F. lost virtually all (>95%) ClO2 at about 112 days.

The following Table 1 shows retentions of ClO2 in glacial acetic acid versus storage time in days. Initial ClO2 concentrations were 940 ppm for room temperature and 1160 ppm for elevated temperature. Elevated temperature was maintained at 120° F. from initiation through Day 154, then the temperature was changed to 105° F. through Day 280 (for reasons unrelated to this experiment).

TABLE 1

| | Days | | | | | | | | | | |
|---|---|---|---|---|---|---|---|---|---|---|---|
| | 14 | 25 | 35 | 56 | 109 | 112 | 154 | 196 | 238 | 280 | 322 |
| % Retention - RT | — | 86.5 | — | 88.3 | — | 90.1 | 89.7 | 90.4 | 90.8 | 90.1 | 86.5 |
| % Retention - Elev. temp | 94.5 | — | 96.6 | — | 94.3 | — | 89.9 | 95.4 | 96.6 | 87.4 | — |

The following Table 2 shows retentions of ClO2 in 10% acetic acid at 120 F versus storage time in days. Initial ClO2 concentrations were 2017 ppm.

TABLE 2

| | Days | | | | | | | |
|---|---|---|---|---|---|---|---|---|
| | 1 | 3 | 7 | 14 | 24 | 56 | 80 | 112 |
| % Retention at 120 F. | 96.5 | 95.9 | 101.0 | 93.1 | 86.4 | 86.3 | 35.2 | 4.5 |

The results of Table 2 represent as good or better stability, at this temperature, compared to any other predominantly aqueous system yet observed, though substantially less stable than the glacial acetic acid system. It is anticipated that intermediate acetic acid/water systems will show progressively greater stability with increasing acetic acid content.

Solutions of ClO2 in mixtures of acetic acid and water can be prepared by first applying methods of preparing solutions of ClO2 in glacial acetic acid noted previously, followed by addition of the desired amount of water, or ClO2 in nitrogen can be bubbled directly into the acetic acid/water mixture. Alternatively, in some cases solutions of ClO2 in water can be prepared by usual methods, followed by addition of the desired amount of acetic acid.

It might be expected that close chemical analogs of acetic acid, such as formic acid and propionic acid, would also serve as solvents in which ClO2 would be relatively stable. However, this appears not to be the case. Solutions of ClO2 in formic acid and in propionic acid were prepared in the manner described above. Each solution had lost virtually all ClO2 within one week, either when stored at elevated temperature or at room temperature.

The freshly-prepared solution of ClO2 in acetic acid was of high purity, since it was obtained by combining only highly pure ClO2 prepared by OxyChem Method II and acetic acid. Acetic acid is available in food grade, so a solution made with it could be suitable for treatment of drinking water and/or other ingestible materials, as well as for other applications. Acetic acid can be obtained in substantially chemically pure grade, pharmaceutical grade, and/or technical grade.

In certain embodiments, the solution can be quickly and conveniently dispersed directly in water that is desired to be treated, since acetic acid is miscible with water in all proportions. Alternatively, the solution can be dissolved in water to form an aqueous chlorine dioxide solution, which can then be used for treating surfaces, solids, waters, fluids, and/or other materials. For example, aqueous solutions of ClO2 prepared by dissolving the acetic acid solution in water, either the water to be treated or an intermediate solution, can be used for any purpose known in the art for which a simple aqueous solution of comparable ClO2 concentration would be used, insofar as this purpose is compatible with the presence of the acetic acid. These uses can include disinfection and/or deodorization and/or decolorization of: drinking water, waste water, recreational water (swimming pools, etc.), industrial reuse water, agricultural irrigation water, and/or surfaces, such as living tissues (topical applications), foods (produce, meats), and/or inanimate surfaces, etc. That is, chlorine dioxide can be released from a composition that comprises chlorine dioxide dissolved in acetic acid to treat a desired target.

If held in an open container, or a container having a permeable aspect to it, the solution ordinarily experiences an evaporative release of ClO2 gas into the air. Conditions can be selected such that the concentration level of the ClO2 released into the air is suitable to be efficacious for disinfection and/or odor control in the air, and/or disinfection of surfaces and/or materials in contact with the air, where such uses are consistent with the amount of acetic acid vapor that will also be released into the air through its evaporation.

The solution can release ClO2 directly, through direct contact and/or via the gas phase, into other substances. The solution can be admixed with such substances, such as by mixing the solution with the other substances in liquid and/or powdered and/or granular form. The solution can be applied to a surface, and/or if desired can be held against the surface mechanically, as with a patch and/or bandage. The substance receiving the ClO2 from the solution can do so as a treatment of the substance and/or the substance can act as a secondary vehicle for the ClO2. One of these approaches may be particularly suitable in circumstances where the presence of substantial amounts of water must be avoided.

Solutions of ClO2 in acetic acid can be very stable (e.g., can retain approximately 90% of the ClO2 for a period of at least 22 weeks at room temperature and at 120° F.). In fact, over the time period observed to date, the stability at temperatures of 105° F. to 120° F. appear comparable to stability at room temperature. However, it is expected that at sufficiently long time intervals stability at room temperature would prove to be greater than at elevated temperatures. By extension, it is likely that ClO2 might exhibit even greater stability at reduced temperatures. This could be an important benefit where extended storage, possibly extreme extended storage, is desired.

Suitable packages are those that can retain gaseous ClO2 to a degree that provides acceptable overall ClO2 retention, as well as being compatible with acetic acid. Suitable materials to provide high ClO2 retention can include glass, some plastics, and/or unreactive metals such as stainless steel. The final form of the product containing the solution can include any suitable means of dispensing and/or delivery, such as, for example, pouring and/or spraying, and/or any other means known in the art.

A closed container of a solution of ClO2 can quickly attain a concentration in the headspace of the container that is in equilibrium with the concentration in the solution. A high concentration aqueous solution can have an equilibrium headspace concentration that exceeds the explosive limits in air (considered to be about 10% by weight in air). For example, an aqueous solution of ≥7500 ppm ClO2 is believed to have an equilibrium concentration of ClO2 in the air above it (such as of the headspace of a container) of ≥10% at 20° C. However, early indications are that the equilibrium concentration of ClO2 in the air above a solution of ClO2 in acetic acid is lower than the equilibrium concentration in the air above an aqueous solution of the same ClO2 concentration.

This relatively low headspace concentration of ClO2 in equilibrium with liquid-phase ClO2 in acetic acid was indicated by the following experiment. A sample of 11 ml of ClO2 in acetic acid was allowed to equilibrate at room temperature in a sealed septum bottle having a total internal volume of about 120 ml. The solution was then withdrawn via syringe needle so that the headspace concentration remained essentially undisturbed, and the solution was measured as 2630 ppm. Then 11 ml of water was injected back into the septum bottle, and the bottle was chilled at about 3° C., allowing the ClO2 in the headspace to dissolve in the chilled water. This water was then withdrawn by syringe and measured as 144 ppm. The ratio 144/2630=0.055 represents a pseudo partition coefficient for ClO2 between air and acetic acid. When this experiment was repeated using an aqueous ClO2 solution in place of the acetic acid solution, the pseudo partition coefficient obtained was 0.32. Since this pseudo partition coefficient for water is significantly larger than that for acetic acid (nearly six-fold), it is believed that acetic acid has a lower equilibrium headspace ClO2 concentration at a given solution concentration.

This suggests that higher concentrations of ClO2 in acetic acid can be handled more safely than equal concentrations of ClO2 in water, in regard to headspace ClO2 concentration.

DEFINITIONS

When the following terms are used substantively herein, the accompanying definitions apply. These terms and definitions are presented without prejudice, and, consistent with the application, the right to redefine these terms during the prosecution of this application or any application claiming priority hereto is reserved. For the purpose of interpreting a claim of any patent that claims priority hereto, each definition (or redefined term if an original definition was amended during the prosecution of that patent), functions as a clear and unambiguous disavowal of the subject matter outside of that definition.

a—at least one.
acetic acid—an organic chemical compound, sometimes represented as CH3COOH, and often considered to be one of the simplest carboxylic acids.
activity—an action, act, step, and/or process or portion thereof.
adapted to—made suitable or fit for a specific use or situation.
air—the earth's atmospheric gas.
and/or—either in conjunction with or in alternative to.
apparatus—an appliance or device for a particular purpose
apply—to place in contact with and/or close physical proximity to and/or to lay and/or spread on.
approximately—about and/or nearly the same as.
aqueous—related to and/or containing water
at least—not less than.
bond—to attach and/or fasten.
can—is capable of, in at least some embodiments.
chlorine dioxide—a highly reactive oxide of chlorine with the formula ClO2 or $ClO_2$, it can appear as a reddish-yellow gas that crystallizes as orange crystals at −59° C., and it is a potent and useful oxidizing agent often used in water treatment and/or bleaching.
closed—having boundaries, enclosed.
combine—to join, unite, mix, and/or blend.
complex—a compound comprising a reversible association of molecules, atoms, and/or ions.
composition of matter—a combination, reaction product, compound, mixture, formulation, material, and/or composite formed by a human and/or automation from two or more substances and/or elements.
compound—composed of two or more substances, parts, elements, and/or ingredients.
comprising—including but not limited to, what follows.
concentration—measure of how much of a given substance there is mixed, dissolved, contained, and/or otherwise present in and/or with another substance.

container—an enclosure adapted to retain a filling and having a closable opening via which a filling can be introduced. Examples of a container include a vial, syringe, bottle, flask, etc.
covalently—characterized by a combination of two or more atoms by sharing electrons so as to achieve chemical stability under the octet rule. Covalent bonds are generally stronger than other bonds.
deliver—to provide, carry, give forth, and/or emit.
device—a machine, manufacture, and/or collection thereof.
dissolve—to make a solution of, as by mixing with a liquid and/or to pass into solution.
dry—(v) to lose and/or remove moisture from; (adj) substantially free from moisture or excess moisture; not moist; not wet.
food grade—determined by the US Food and Drug Administration as safe for use in food.
form—(v) to construct, build, generate, and/or create; (n) a phase, structure, and/or appearance.
from—used to indicate a source.
further—in addition.
greater—larger and/or more than.
initial—at a beginning.
may—is allowed and/or permitted to, in at least some embodiments.
method—a process, procedure, and/or collection of related activities for accomplishing something.
mix—to combine (substances, elements, things, etc.) into one mass, collection, or assemblage, generally with a thorough blending of the constituents.
molar ratio—the ratio of moles of one substance to moles of another substance.
not—a negation of something.
pharmaceutical grade—determined by the US Food and Drug Administration as safe for use in drugs.
plurality—the state of being plural and/or more than one.
polymer—any of numerous natural and synthetic compounds of usually high molecular weight consisting of up to millions of repeated linked units, each a relatively light and simple molecule.
precipitate—a substance separated in solid form and/or phase from a solution.
predetermined—established in advance.
probability—a quantitative representation of a likelihood of an occurrence.
release—to let go and/or free from something that restrains, binds, fastens, and/or holds back.
repeatedly—again and again; repetitively.
result—an outcome and/or consequence of a particular action, operation, and/or course.
retain—to restrain, keep, and/or hold.
said—when used in a system or device claim, an article indicating a subsequent claim term that has been previously introduced.
separate—to disunite, space, set, or keep apart and/or to be positioned intermediate to.
set—a related plurality.
solid—neither liquid nor gaseous, but instead of definite shape and/or form.
solution—a substantially homogeneous molecular mixture and/or combination of two or more substances.
store—to take in, hold, and/or secure.
substantially—to a great extent or degree.
substrate—an underlying layer.
surface—the outer boundary of an object or a material layer constituting or resembling such a boundary.
system—a collection of mechanisms, devices, machines, articles of manufacture, processes, data, and/or instructions, the collection designed to perform one or more specific functions.
technical grade—containing small amounts of other chemicals, hence slightly impure.
temperature—measure of the average kinetic energy of the molecules in a sample of matter, expressed in terms of units or degrees designated on a standard scale.
utilize—to use and/or put into service.
via—by way of and/or utilizing.
water—a transparent, odorless, tasteless liquid containing approximately 11.188 percent hydrogen and approximately 88.812 percent oxygen, by weight, characterized by the chemical formula $H_2O$, and, at standard pressure (approximately 14.7 psia), freezing at approximately 32° F. or 0 C and boiling at approximately 212° F. or 100 C.
weight—a force with which a body is attracted to Earth or another celestial body, equal to the product of the object's mass and the acceleration of gravity; and/or a factor assigned to a number in a computation, such as in determining an average, to make the number's effect on the computation reflect its importance.
when—at a time.
wherein—in regard to which; and; and/or in addition to.
with respect to—in relation to.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:
 there is no requirement for the inclusion of any particular described or illustrated characteristic, function, activity, or element, any particular sequence of activities, or any particular interrelationship of elements;
 any elements can be integrated, segregated, and/or duplicated;
 any activity can be repeated, any activity can be performed by multiple entities, and/or any activity can be performed in multiple jurisdictions; and
 any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive.

What is claimed is:

1. An acidic composition of matter comprising:
   chlorine dioxide dissolved in acetic acid, the acetic acid having a concentration of at least 75% by weight.
2. The composition of matter of claim 1, wherein:
   a concentration of said dissolved chlorine dioxide is at least 10 ppm.
3. The composition of matter of claim 1, wherein:
   a concentration of said dissolved chlorine dioxide is up to 2000 ppm.
4. The composition of matter of claim 1, wherein:
   said acetic acid is aqueous.
5. The composition of matter of claim 1, wherein:
   with the exception of said chlorine dioxide, said acetic acid is substantially pure.
6. The composition of matter of claim 1, wherein:
   when stored, a concentration of chlorine dioxide in said composition of matter is retained, with respect to an initial concentration of chlorine dioxide in said composition of matter, at greater than 30% for at least 28 days.
7. The composition of matter of claim 1, wherein:
   when stored, a concentration of chlorine dioxide in said composition of matter is retained, with respect to an initial concentration of chlorine dioxide in said composition of matter, at greater than 80% for at least 150 days.
8. The composition of matter of claim 1, wherein:
   when stored in a closed container at a temperature of approximately 120 F or lower, a concentration of chlorine dioxide in said composition of matter is retained, with respect to an initial concentration of chlorine dioxide in said composition of matter, at greater than 30% for at least 28 days.
9. The composition of matter of claim 1, wherein:
   when stored in a closed container at a temperature of approximately 120 F or lower, a concentration of chlorine dioxide in said composition of matter is retained, with respect to an initial concentration of chlorine dioxide in said composition of matter, at greater than 90% for at least 100 days.
10. The composition of matter of claim 1, wherein:
    when stored in a closed container at room temperature, a concentration of chlorine dioxide in said composition of matter is retained, with respect to an initial concentration of chlorine dioxide in said composition of matter, at greater than 86% for at least 25 days.
11. The composition of matter of claim 1, wherein:
    said acetic acid is substantially chemically pure.
12. The composition of matter of claim 1, wherein:
    said acetic acid is pharmaceutical grade.
13. The composition of matter of claim 1, wherein:
    said acetic acid is food grade.
14. The composition of matter of claim 1, wherein:
    said acetic acid is technical grade.
15. A method comprising:
    dissolving chlorine dioxide in an acetic acid solution, the acetic acid having a concentration of at least 75% be weight.
16. A method comprising:
    dissolving chlorine dioxide in an aqueous acetic acid solution containing at least 75% be weight acetic acid to form an acidic composition of matter; and
    storing said composition of matter for at least 28 days.
17. A method comprising:
    combining an aqueous chlorine dioxide solution with acetic acid and/or aqueous acetic acid solution to form an acidic combined solution containing at least 75% be weight acetic acid; and
    storing said combined solution for at least 28 days.
18. A method comprising:
    storing, in a closed container, an acidic composition of matter comprising chlorine dioxide dissolved in acetic acid, the acetic acid having a concentration of at least 75% be weight, a concentration of chlorine dioxide in said composition of matter retained, with respect to an initial concentration of chlorine dioxide in said composition of matter, at greater than 30% for at least 28 days.
19. The method of claim 18, further comprising:
    applying said composition of matter to water.
20. The method of claim 18, further comprising:
    applying said composition of matter to a surface.
21. The method of claim 18, further comprising:
    applying said composition of matter to air.
22. A method comprising:
    releasing chlorine dioxide from an acidic composition comprising chlorine dioxide dissolved in acetic acid, the acetic acid having a concentration of at least 75% be weight.

* * * * *